United States Patent

Ogata et al.

Patent Number: 4,687,831
Date of Patent: Aug. 18, 1987

[54] ANTITHROMBOGENIC SYNTHETIC ELASTOMER AND PROCESS OF PREPARATION THEREOF

[75] Inventors: Naoya Ogata; Kohei Sanui; Nobuhiko Yui, all of Tokyo; Kazuhiko Nojima, Kanagawa; Kazunori Kataoka, Tokyo; Teruo Okano, Chiba; Yasuhisa Sakurai, Tokyo, all of Japan

[73] Assignee: Research Development Corp. of Japan, Tokyo, Japan

[21] Appl. No.: 852,656

[22] Filed: Apr. 16, 1986

[30] Foreign Application Priority Data

Apr. 26, 1985 [JP] Japan .................................. 60-88857

[51] Int. Cl.$^4$ ............................................. C08G 18/10
[52] U.S. Cl. ......................................... 528/64; 528/76
[58] Field of Search ..................................... 528/64, 76

[56] References Cited

U.S. PATENT DOCUMENTS 3,188,302  6/1965  Lorenz .................................. 528/63
3,926,922 12/1975  Banon et al. .......................... 528/64

Primary Examiner—Maurice J. Welsh
Attorney, Agent, or Firm—Stephen F. K. Yee

[57] ABSTRACT

Antithrombogenic synthetic elastomer having repeat units comprising portion I which is a soft segment unit containing a polyether and portion II which is a hard segment unit:

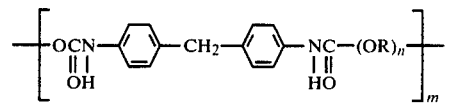

I

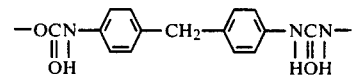

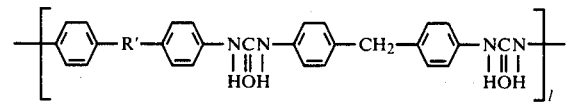

II

R is a straight-chain or branched-chain alkylene group containing 2 to 4 carbon atoms, R' is amide a urethane, an urea, n ranges up to 180, m is an integer of 1 to 20, l is an integer of 1 to 10, said polymer having a microdomain structure composed of soft and hard segments, the domains of which have an average size of 10 to 20 nm, and a molecular weight of about 80,000 to about 500,000.

The polymer shows little adhesion of blood platelets thereto, little deformation of adhering blood platelets and an excellent antithrombogenic property. This polymer has excellent mechanical properties as an elastomer. This polymer is useful for artificial organs such as blood vessels, kidneys, hearts, and for functional biomaterials and devices such as absorbents for biological components, carriers for sustained release preparations, adhesive materials for living tissue, injectors, blood bags and catheters.

12 Claims, 1 Drawing Figure

ANTITHROMBOGENIC SYNTHETIC ELASTOMER AND PROCESS OF PREPARATION THEREOF

BACKGROUND OF THE INVENTION

(1) Technical Field

The present invention relates to an antithrombogenic synthetic elastic polymer, particularly to an antithrombogenic block copolymer composed of soft segment chains and hard segment chains.

(2) Background Information

The so-called antithrombogenic materials which eliminate interaction with blood should be developed, because of their necessity in fabricating the high functional artificial organs, including artificial blood vessels or artificial kidneys. At present, the artificial hearts of the permanent implantable type are partly utilized. When they are used for a long term, it is important to have both a reliable compatibility with blood or tissues, and a favorable biological stability. However, any material which affords full satisfaction to these problems has not yet been obtained. Particularly, the development of excellent biomaterials which could be used in direct contact with blood is urgently demanded.

SUMMARY OF THE INVENTION

It is therefore a primary object of the present invention to provide an antithrombogenic material consisting of a synthetic polymer alone, which is excellent in antithrombogenic and mechanical properties.

For the purpose of achieving the above-mentioned object, the present inventors have studied adhesion phenomena of blood platelets to the surfaces of various materials. As a result, it has been found that the problems described above are solved by a polymer having both soft segment units containing a polyether and hard segment units, thus arriving at the present invention.

In accordance with the present invention, there is provided an antithrombogenic synthetic elastomer having repeat structural units represented by the following structural formula comprising portions I and II:

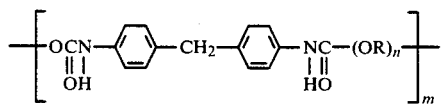

I

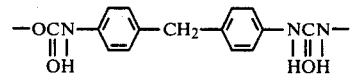

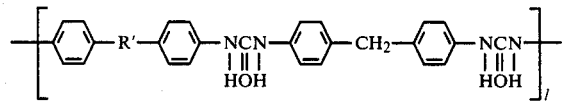

II wherein R is a straight-chain or branched-chain alkylene group containing from 2 to 4 carbon atoms, R' is an amide group, a urethane group, a urea group or the like, n ranges up to 180, preferably up to 30, m is an integer of 1 to 20, preferably 1 to 10, and l is an integer of 1 to 10, preferably 1 to 5, said polymer having a microdomain structure composed of the soft and hard segments, the domains of which have an average size of 10 to 20 nm, and a molecular weight of said polymer being in the range of about 80,000 to about 500,000.

DESCRIPTION OF THE PREFERRED EMBODIMENTS

Figure 1:
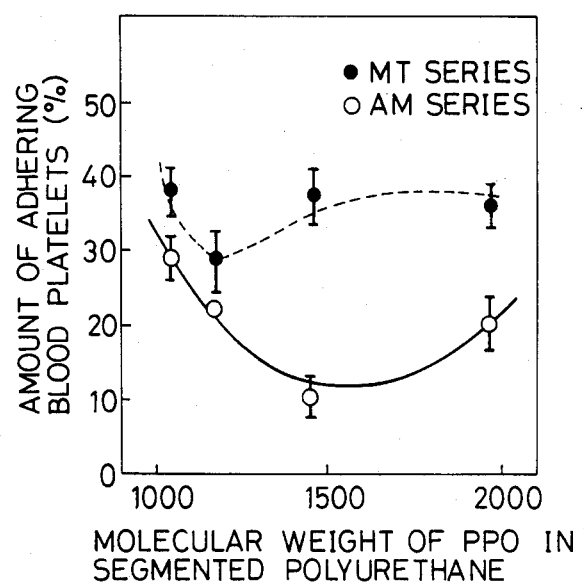
FIG. 1 is a graph showing relationships between molecular weights of poly(propylene oxide) (PPO) in a segmented polyurethane of the present invention, wherein R' is an amide group (AM series), and amount of adhering blood platelets thereto; and a similar relationship between a segmented polyurethane, wherein R' is a methylene group (MT series, comparison test), and amount of adhering blood platelets thereto.

The portion I of the structural formula represents a repeat unit comprising a polyether and urethane linkages. On the other hand, the portion II of the structural formula represents a repeat unit of a polyurea. The portions I and II of the structural formula are connected to each other by an urethane linkage.

In the portion I of the structural formula, R is a straight-chain or branched-chain alkylene group containing from 2 to 4 carbon atoms, such as ethylene group, isopropylene group or tetramethylene group, and n ranges up to 180, preferably up to 30, although n is not particularly limited.

The microdomain structure of the portion II of the structural formula, the portion II being namely a polyurea, varies with the change of R'. R' is not particularly limited and includes an amide group, a urethane group, a urea group and the like. The preferred group is an amide group.

The polymer is characterized by the microdomain structure composed of the soft and hard segments, the domains of which have an average size of 10 to 20 nm. This size is variously changeable with the polymerization ratio of the portions I and II of the structural formula.

The average size of the hard segment domain was obtained by extrapolating the size of the soft segments to zero in the average repeat size of the soft and hard segment domains measured with a small angle X-ray scattering.

Although m is not particularly limited, m is in the range of 1 to 20, preferably in the range of 1 to 10. Further, l is in the range of 1 to 10, preferably in the range of 1 to 5.

There is not particularly limited the quantitative relationship between the portions I and II of the structural formula, but it is preferable that the portion I is contained in an amount of 40 to 80% by weight.

While the antithrombogenic synthetic elastomer of the present invention can be synthesized by various processes, it is usually produced by reacting a polyether with a diisocyanate to synthesize a prepolymer in which isocyanate groups are introduced to both ends of the polyether included in the portion I of the structural formula described above, and thereafter reacting the prepolymer with the diisocyanate and a diamine to polyadd them, in order to form the portion II of the structural formula.

The synthetic polymer of the present invention thus obtained is a multi-block copolymer.

The polyether which is the raw material compound mentioned above includes, for example, poly(ethylene oxide), poly(propylene oxide), poly(tetramethylene oxide) and the like.

The examples of the antithrombogenic synthetic elastomer of the present invention are shown as follows:

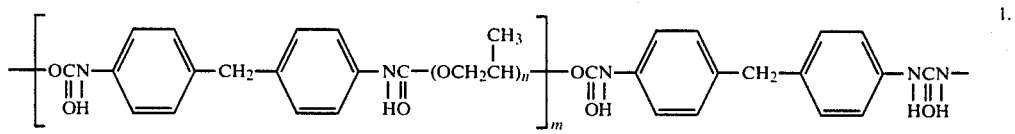

I

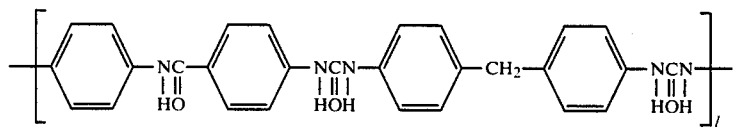

II

As the diisocyanate, there can be mentioned 4,4'-diphenylmethane diisocyanate, 4,4'-dicyclohexylmethane diisocyanate, hexamethylene-1,6-diisocyanate and the like.

Wherein n ranges up to 180, m is an integer of 1 to 20 and l is an integer of 1 to 10.

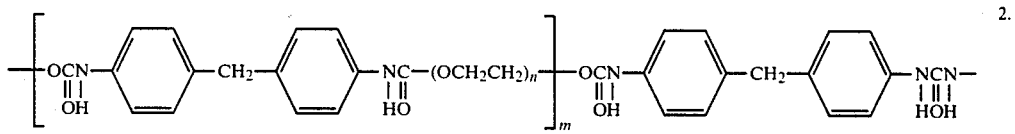

I

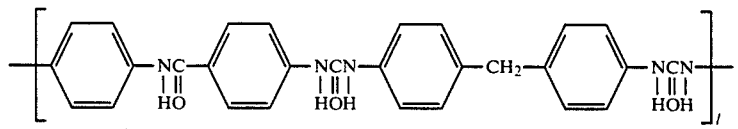

II wherein n ranges up to 180, m is an integer of 1 to 20 and l is an integer of 1 to 10.

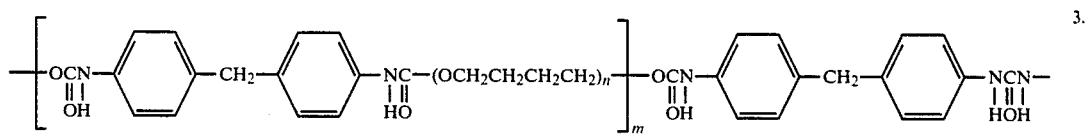

I

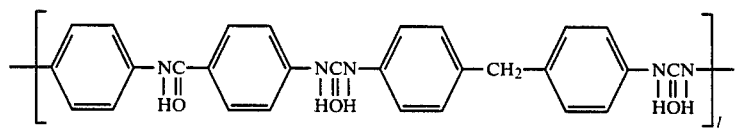

II

The diamine includes 4,4'-diaminobenzanilide, 4,4'-diamino-diphenylurea, 4,4'-diaminodiphenylurethane and the like.

wherein n ranges up to 100, m is an integer of 1 to 20 and l is an integer of 1 to 10.

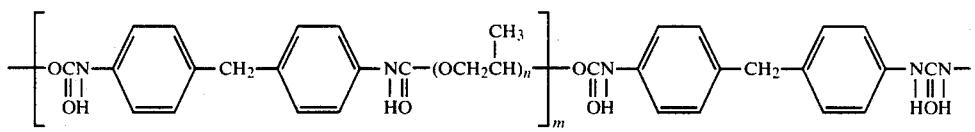

I

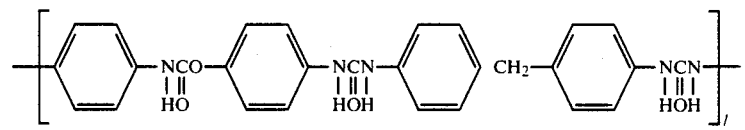

II wherein n ranges up to 180, m is an integer of 1 to 20 and l is an integer of 1 to 15.

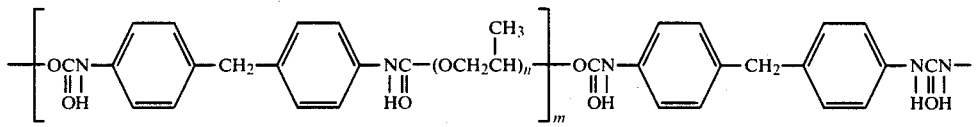

I

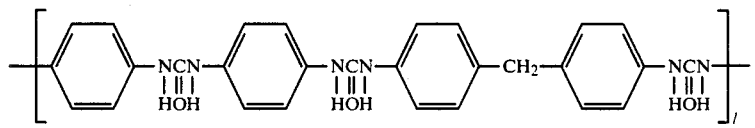

II wherein n ranges up to 180, m is an integer of 1 to 20 and l is an integer of 1 to 10.

The antithrombogenic synthetic polymer of the present invention can be used for artificial organs including artificial blood vessels, artificial kidneys and the like, which are employed in contact with blood, and for functional biomaterials and devices such as absorbents for biological components, carriers for sustained release preparations, adhesive materials for living tissue, injectars, blood bags, catheters and the like.

First, the synthetic polymer of the present invention shows a very excellent antithrombogenic property. That is to say, it is observed that the adhesion of blood platelets to the polymer surface is extremely little and the deformation of adhering blood platelets scarcely occurs. From these results, it is seen that this synthetic polymer has an excellent antithrombogenic property.

Secondly, this synthetic polymer shows excellent mechanical properties such as a high mechanical strength, a high elasticity and a high elongation. It is also appreciated that this polymer has a high wear resistance to withstand repeating deformation, which is required for artificial hearts and the like.

Thirdly, the microdomain structure composed of soft segments and hard segments can be controlled by the variation of the quantitative relationship between the portions I and II of the structural formula, and the antithrombogenic property of the materials can be easily improved by this microdomain structure.

Methods for using the synthetic polymer of the present invention as antithrombogenic materials will hereinafter be described.

When this synthetic polymer is used as artificial blood vessels, artificial kidneys, artificial hearts, absorbents for biological components, carriers for sustained release preparations, its functions can be shown by shaping it in desired forms. For example, when it is desired to cast the polymer in a film form, the polymer can be casted in a desired thickness with the polymer solution. Further, the polymer can be molded in the other forms by plasticizing with heat and the like.

Furthermore, the functions of the present invention can also be shown by the technique in which this synthetic polymer is applied on the conventional polymers, without using this synthetic polymer for the structural members as it is. The synthetic polymer of the present invention attains the superiority over natural materials in shaping thereof.

The synthetic polymer of the present invention has both the portion I, namely the polyether portion, and the portion II connected thereto by the urethane linkage, namely the polyurea portion. The polymer has, therefore, the microdomain structure which has the softness of the polyether as the soft segments and the rigidity of the polyurea as the hard segments. As a consequence, the polymer has the functions that not only an excellent molding ability, processability and durability are given, but also the antithrombogenic property can be improved.

The present invention will now be described in detail with reference to the following examples that by no means limit the scope of the invention.

EXAMPLE 1

Poly(propylene oxide) (PPO) having a number average molecular weight of 1,500 and 4,4'-diphenylmethane diisocyanate were reacted with each other at a mole ratio of 4,4'-diphenylmethane diisocyanate to PPO of 2:1 under an atmosphere of nitrogen at a temperature of 80° to 90° C. for 8 hours, and thereby there was synthesized PPO having the isocyanate groups at both ends thereof. This reaction product was dissolved in N-methyl-2-pyrrolidone (NMP) after being cooled to room temperature. 4,4'-diaminobenzanilide dissolved in a 7 weight % NMP-lithium chloride solution was added dropwise to it and then stirred at room temperature (18° C.). Consequently, the solution polymerization was carried out and the synthetic polymer was obtained.

This synthetic polymer had the following repeat structural unit:

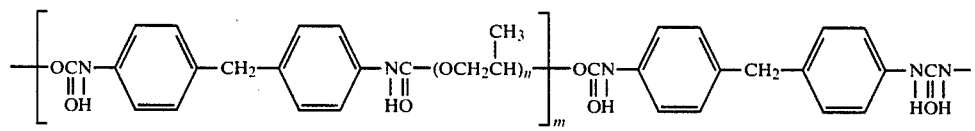

I

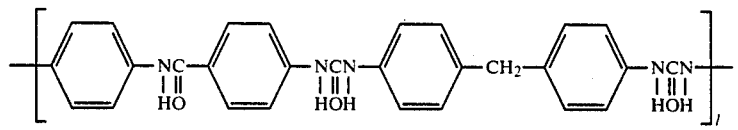

II wherein n was 26, m was about 10 and l was about 5. The molecular weight of this polymer was about 120,000 and the PPO content of this polymer was 67%.

EXAMPLE 2

Poly(propylene oxide) (PPO) having a number average molecular weight of 2,000 and 4,4'-diphenylmethane diisocyanate were reacted with each other at a mole ratio of 4,4'-diphenylmethane diisocyanate to PPO of 2:1 under an atmosphere of nitrogen at a temperature of 80° to 90° C. for 8 hours, and thereby PPO having the isocyanate groups at both ends thereof was synthesized. This reaction product was dissolved in NMP after being cooled to room temperature. 4,4'-diaminobenzanilide dissolved in a 7 weight % NMP-lithium chloride solution was added dropwise to it and then stirred at room temperature (18° C.). Consequently, the solution polymerization was carried out and the synthetic polymer was obtained.

This synthetic polymer had the following repeat structural unit:

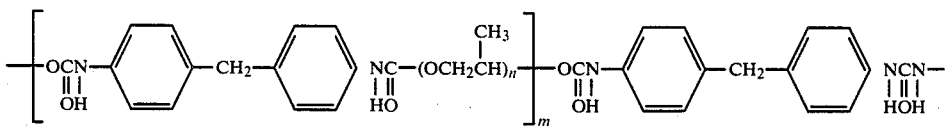

I

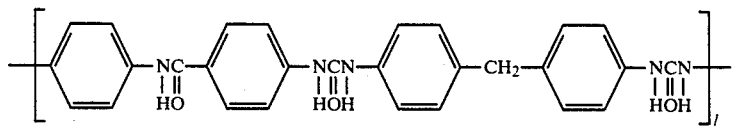

II wherein n was 26, m was about 10 and l was 5. The molecular weight of this polymer was about 150,000 and the PPO content of this polymer was 80%.

EXAMPLE 3

The same experiment as that of Example 1 was carried out, with the exception that PPO in Example 1 was substituted for poly(ethylene oxide) (PEO) having a number average molecular weight of 1,500. The synthetic polymer thus obtained had the following repeat structural unit:

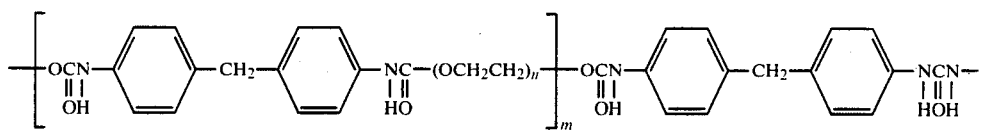

I

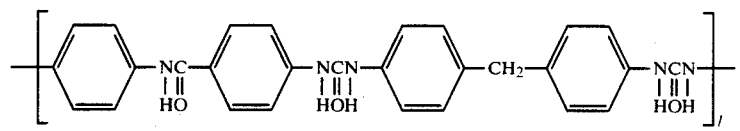

II wherein n was 34, m was 15 and l was 5. The molecular weight of this polymer was about 100,000 and the PEO content of this polymer was 70%.

EXAMPLE 4

The same experiment as that of Example 1 was carried out, with the exception that PPO in Example 1 was substituted for poly(tetramethylene oxide) (PTMO) having a number average molecular weight of 1,500. The synthetic polymer thus obtained had the following repeat structural unit:

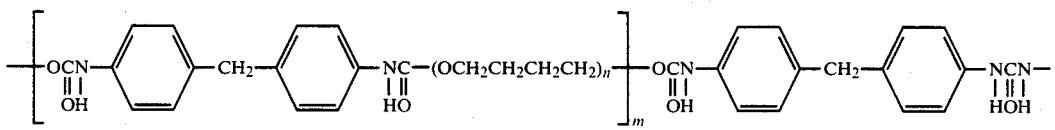

I

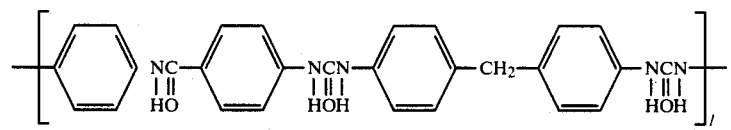

II wherein n was 20, m was 5 and l was 5. The molecular weight of this polymer was 150,000 and the PTMO content of this polymer was 67%.

The structure identification of the synthetic polymers obtained in Examples 1 through 4 was carried out as follows.

The formation of the polyether having the isocyanate groups at both ends thereof synthesized by the reaction of the polyether with the diisocyanate was identified by the infrared adsorption spectrum (IR). That is to say, by the reaction, the absorption at 3470 cm$^{-1}$ caused by the end hydroxyl group of the polyether disappeared, and, instead of it, the absorption at 1740 cm$^{-1}$ caused by the urethane group was observed.

The synthesis of the copolymer by the reaction of the product described above with the diamine was identified by the infrared absorption spectrum (IR). Namely, by the reaction, the absorption at 2260 cm$^{-1}$ caused by the isocyanate group disappeared, and, instead of it, the absorption at 1640 cm$^{-1}$ caused by the urea group was observed. The absorption at 1740 cm$^{-1}$ caused by the urethane group corresponding to the connecting part of the portion I and the portion II of the structural formula was observed as it was.

Because this synthetic polymer was purified by the use of methanol which was a good solvent for the polyether, it was decided that this synthetic polymer had the prescribed structure.

EXAMPLE 5

The polymers prepared in Examples 1 and 2 were dissolved in an amount of 1.3 g in 25 ml of m-cresol, respectively, and were cast in a film form by using a flat dish to prepare 5 mm×50 mm strips. The stress-strain behavior and the hysteresis of the film strips thus prepared were determined at a temperature of 25° C., at a gauge distance of 20 mm, and at a tensile rate of 300 mm/min. The polymer prepared in Example 1 had a Young's modulus of 1.3 to 2 times that of the polymer wherein R' was a methylene group, and showed a lower value of 50 to 60% in hysteresis.

EXAMPLE 6

Glass beads having a size in the range of 48 to 60 meshes were washed with a potassium hydroxide-sodium hydroxide-methanol aqueous solution and water, and then were dried in vacuo. Ten grams of the washed glass beads were immersed in 10 ml of m-cresol solutions in which the polymers prepared in Examples 1 to 4 were dissolved in an amount of 50 mg, respectively. After being stirred at room temperature for one hour, they were filtered and dried under reduced pressure at 60° C. for 48 hours.

By using the glass beads thus coated with the polymers, the following experiments were carried out. The glass beads described above were densely packed in polyvinyl chloride tubing of 3 mm diameter and 10 cm length, and fresh blood collected from the jugular vein of a mongrel adult dog was passed therethrough at a flow rate of 0.4 ml/min for one minute.

The polymers prepared in Examples 1 and 2 showed excellent values of 10% and 25%, respectively, in a ratio of sticked blood platelets. In the polymer prepared in Example 1, the sticked blood platelets well retained their original form.

EXAMPLE 7

In FIG. 1, there were shown relationships between molecular weights of PPO in the elastic polymers having repeat structural units represented by the formula described hereinbefore, wherein R was a propylene group, and ratios of adhering blood platelets thereto. For comparison, the relationships were indicated with respect to the polymer wherein R' was —CH$_2$— (MT series, Comparison Example) and the polymer wherein R' was

(AM series).

The polymer of the MT series showed amount of adhering blood platelets of 30 to 40%, and gave a minimum value in the vicinity of a molecular weight of PPO of 1,200. On the contrary, the polymer of the AM series which had an amide linkage showed a relatively low amount of adhering blood platelets. Particularly, the polymer including PPO having a molecular weight of 1,450 caused the adhesion of blood platelets to be minimized, showing an extremely low value of about 10% in amount of adhering blood platelets. The good compatibility of the AM series polymer for blood appears to be affected by the microdomain structure of the polymer surface.

What is claimed is:

1. An antithrombogenic synthetic elastomer having repeat structural units represented by the following structural formula comprising portions I and II:

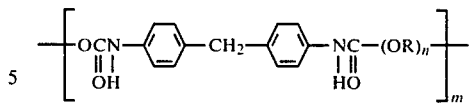

I

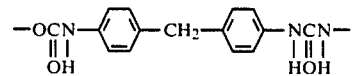

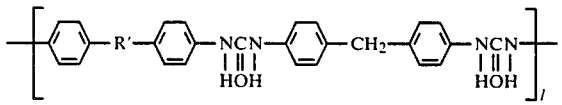

II wherein R is a straight-chain or branched-chain alkylene group containing from 2 to 4 carbon atoms, R' is an amide group, a urethane group, or a urea group, n ranges up to 180, m is an integer of 1 to 20, and l is an integer of 1 to 10, said polymer having a microdomain structure comprised of the segments I and II, the domains of which have an average size of 10 to 20 nm, and the molecular weight of said polymer being in the range of about 80,000 to about 500,000.

2. An antithrombogenic synthetic elastomer according to claim 1, wherein R is selected from the group consisting of

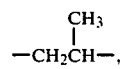

—CH$_2$CH$_2$— and —CH$_2$CH$_2$CH$_2$CH$_2$—, and R' is

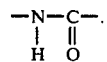

3. An antithrombogenic synthetic elastomer according to claim 1, wherein said polymer has repeat structural units represented by the following structural formula:

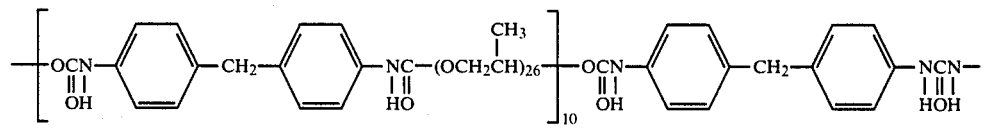

I

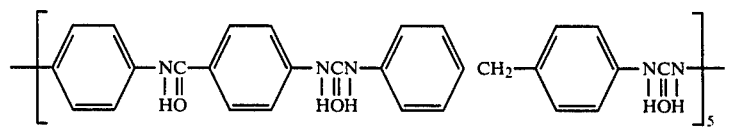

II the molecular weight of said polymer is about 120,000, and the poly(propylene oxide) content therein is 67%.

4. An antithrombogenic synthetic elastomer according to claim 1, wherein said polymer has repeat structural units represented by the following structural formula:

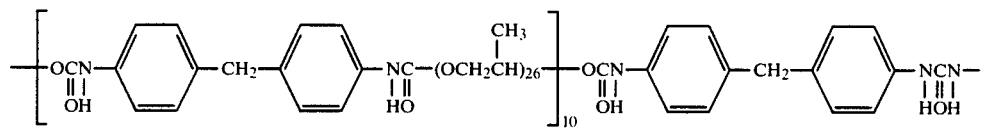

I

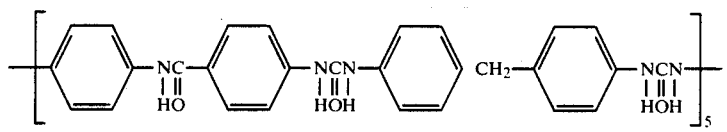

II the molecular weight of said polymer is about 150,000, and the poly(propylene oxide) content therein is 80%.

5. An antithrombogenic synthetic elastomer according to claim 1, wherein said polymer has repeat structural units represented by the following structural formula:

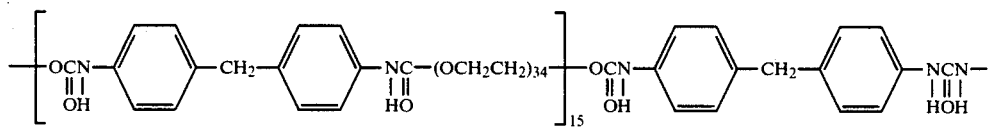

I

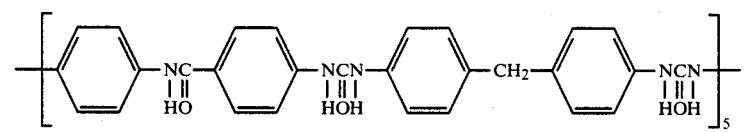

II the molecular weight of said polymer is about 100,000, and the poly(ethylene oxide) content therein is 70%.

6. An antithrombogenic synthetic elastomer according to claim 1, wherein said polymer has repeat structural formula:

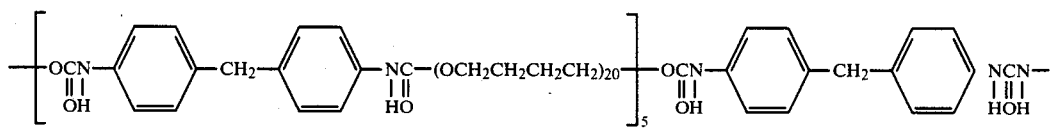

I the molecular weight of said polymer is about 150,000, and the poly(tetramethylene oxide) content therein is 67%.

7. A process for preparing an antithrombogenic synthetic elastomer having repeat structural units represented by the following structural formula comprising portions I and II:

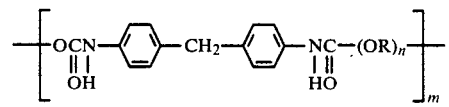

I

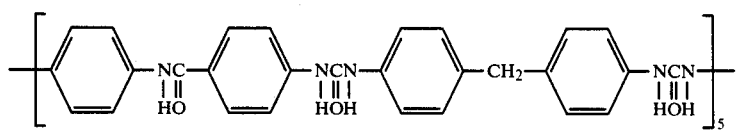

II

-continued

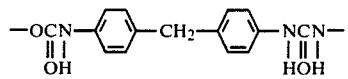

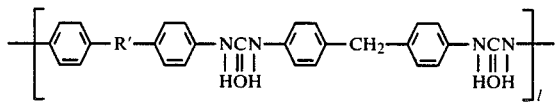

wherein R is a straight-chain or branched-chain alkylene group containing from 2 to 4 carbon atoms, R' is an amide group, a urethane group, or a urea group, n ranges up to 180, m is an integer of 1 to 20 and l is an integer of 1 to 10, said polymer having a microdomain structure comprised of segments I and II, the domains of which have an average size of 10 to 20 nm, and the molecular weight of said polymer being in the range of about 80,000 to about 500,000, which comprises the steps of reacting a polyether with a diisocyanate to obtain a prepolymer in which isocyanate groups are introduced to both ends of the polyether included in the portion I of said structural formula, and thereafter addition polymerizing said prepolymer with the diisocyanate and a diamine.

8. A process for preparing an antithrombogenic synthetic elastomer according to claim 7, wherein said polyether is selected from the group consisting of poly(ethylene oxide), poly(propylene oxide) and poly(tetramethylene oxide).

9. A process for preparing an antithrombogenic synthetic elastomer according to claim 7, wherein said diisocyanate is 4,4'-diphenylmethane diisocyanate.

10. A process for preparing an antithrombogenic synthetic elastomer according to claim 7, wherein said diamine is 4,4'-diaminobenzanilide.

11. An antithrombogenic synthetic elastomer according to claim 3, wherein the molecular weight of the poly(propylene oxide) is in a range of 1450–1500.

12. An antithrombogenic synthetic elastomer according to claim 4, wherein the molecular weight of the poly(propylene oxide) is in a range of 1450–1500.

* * * * *